United States Patent [19]

Drouin

[11] Patent Number: 5,322,788
[45] Date of Patent: Jun. 21, 1994

[54] **MONOCLONAL ANTI-BODY TO CELL SURFACE PROTEIN OF THE BACTERIUM *STREPTOCOCCUS PNEUMONIAE***

[75] Inventor: Josée Drouin, Ottawa, Canada

[73] Assignee: Global Tek, Inc., Bellingham, Wash.

[21] Appl. No.: 865,468

[22] Filed: Apr. 9, 1992

[51] Int. Cl.$^5$ ............ C12N 5/12; C12N 5/20; A61K 39/40; C07K 15/28
[52] U.S. Cl. ............ 435/240.27; 530/388.4; 530/389.5; 424/92; 435/7.34; 435/70.21; 435/885
[58] Field of Search ............ 424/92; 435/7.34, 70.21, 435/885, 240.27; 530/388.4, 389.5

[56] References Cited

PUBLICATIONS

McDaniel et al., Inf. Imm., vol. 59 No. 1, pp. 222–228, 1991.
Charron et al., PNAS, vol. 76, No. 12, pp. 6567–6571 1979.
Crain et al., Infection and Immunity, vol. 58 Oct. 1990, pp. 3293–3299.
McDaniel et al., Infection and Immunity Nov. 1988, pp. 3001–3003.
Fazekas De St. Groth and Scheidegger, *Journal of Immunological Methods,* vol. 35, 1–21 (1980).
Brodeur et al, *Journal of Immunological Methods,* vol. 71, 265–272 (1984).
Brodeur et al, *Journal of Medical Microbiology,* vol. 15, 1–9 (1982).
Laemmli, *Nature,* vol. 227, 680–685 (1970).
Weber and Osborn, *Journal of Biological Chemistry,* vol. 244, 4406–4412 (1969).
Towbin et al, *Proceedings of the National Acad. Sci.,* vol. 76, 4350–4354 (1979).

*Primary Examiner*—Christina Y. Chan
*Assistant Examiner*—Ron Schwadron
*Attorney, Agent, or Firm*—Foley & Lardner

[57] ABSTRACT

This invention relates to a monoclonal antibody (MAb) directed against a surface protein of *Streptococcus pneumoniae,* a hybridoma cell line producing said antibody, and the use of such an antibody to detect the bacterium *Streptococcus pneumoniae,* or to detect antigens of *Streptococcus pneumoniae.*

2 Claims, No Drawings

MONOCLONAL ANTI-BODY TO CELL SURFACE PROTEIN OF THE BACTERIUM *STREPTOCOCCUS PNEUMONIAE*

BACKGROUND OF THE INVENTION

The present invention involves a monoclonal antibody (MAb) with the specificity for a 67,000 dalton cell surface protein of *Streptococcus pneumoniae*, a cell line that produces said antibody, and the partially purified 67,000 dalton cell surface protein.

*S.pneumoniae* is the leading cause of community-acquired bacterial pneumonia (pneumococcal disease) with approximately 500,000 cases a year reported in the United States. Bacterial pneumonia is the most prevalent among the very young, the elderly and immunocompromised persons. In infants and children, pneumococci are the most common bacterial cause of pneumonia, otitis media and bacteremia and a less common cause of meningitis (causing 20–25% of reported cases).

Pneumococci are carried in the respiratory tract of a significant number of healthy individuals. In spite of the high carriage rate, its presence does not necessarily imply infection. However, if one of the highly pathogenic pneumococcal types, such as *S.pneumoniae*, is isolated from rusty-coloured sputum (also containing a large number of polymorphonuclear leucocytes), body fluids, blood cultures, or specimens collected via trans-tracheal or lung puncture from the lower respiratory tract, its detection is usually significant.

Detection of this bacteria at an early stage is essential to facilitate treatment of the infection. Thus, it is important to possess the ability to identify whether *S.pneumoniae* is present in a patient and to be able to follow the effect of antibiotic treatment on the bacteria. As available immunoassays for *S.pneumoniae* antigen detection have shown lack of specificity and/or sensitivity, there remains the need for an improved method of such detection.

*S.pneumoniae* is a gram positive bacteria. Proteins located on the cell surface of many gram positive bacteria have, in the past, been used in typing and immunoprotection studies. There are a large number of *S.pneumoniae* strains, and there are many cell surface proteins associated with *S.pneumoniae*. This has made the identification of a common but exclusive cell surface antigen difficult. However, MAb technology has provided researchers with tools to reproducible and accurately analyze the cell surface components of *S.pneumoniae*. In addition, *S.pneumoniae* proteins are of interest to epidemiologists as they may provide for vaccines against the bacteria.

One such pneumonococcal capsular polysaccharide vaccine has been developed, which incorporates the polysaccharide antigen of 23 serotypes of pneumococci that are responsible for 87% of pneumococcal disease in the United States. This second generation vaccine replaced the 14-valent polysaccharide vaccine licensed in 1977. However, the U.S. Department of Health and Human Services states that a more immunogenic pneumococcal vaccine is needed, particularly for children younger than 2 years of age. This is because the 23-valent vaccine is poorly antigenic in this age group, and its use is not recommended in children with recurrent upper respiratory diseases, such as otitis media and sinusitis. Furthermore, the 23-valent vaccine is only 44–61% efficacious when administered to persons over 65 years old, and revaccination is not advised. Thus, there remains the need for an improved pneumococcal vaccine.

It follows then, that there remains a need for at least two products relating to *S.pneumoniae*. The first is a rapid, specific, and sensitive diagnostic technique for of all strains of *S.pneumoniae*, that does not give false positive results. What is optimally desired is a Mab that will recognize a cell surface antigen that is universally present in most, if not all, strains of *S.pneumoniae* and, at the same time does not recognize other organisms or material which may be found in conjunction with *S.pneumoniae*. Secondly, it is desirous that the Mab and said 67,000 dalton protein be used in research towards development of an improved vaccine.

SUMMARY OF INVENTION

The present invention involves a Mab that is reactive with an epitope (an antigenic determinant of known structure) of a proteinaceous surface component of the bacterium *S.pneumoniae*, with said antibody being reactive with said antigen in at least 96% of strains of *S.pneumoniae*.

It is preferred that such MAb is reactive with an epitope of a proteinaceous cell surface component of the bacterium *S.pneumoniae*, particularly a protein of approximately 67,000 daltons.

An additional aspect of this invention involves a cell line capable of producing a MAb that is reactive with an epitope of a proteinaceous cell surface component of the bacterium *S.pneumoniae*, with said epitope being present in at least 96% of strains of said bacterium.

It is preferred that said cell line be capable of generating a MAb that demonstrates specificity for an epitope of a proteinaceous cell surface component of the bacterium *S.pneumoniae*. It is preferred that said cell line is a hybridoma cell line, specifically a hybrid of a mouse spleen cell and an immortal myeloma cell.

A further aspect of this invention provides a diagnostic method to identify, type, and/or detect the presence of the bacterium *S.pneumoniae* or its antigens, with such method (a) causing the test sample to come into contact with said MAb; and (b) observing whether cell-labelling or agglutination occurs, indicating the presence of *S.pneumoniae* or an antigen of *S.pneumoniae*.

It is preferred that such a method involves a MAb that is reactive with an epitope of a proteinaceous cell surface component that is present in at least 96% of the known strains of *S.pneumoniae*. It is additionally preferred that the said label is chosen from a radio-label, a fluorescent label, a colloidal gold label, and a biotin label or an enzyme label. This method could also be employed to detect infection of *S.pneumoniae* in patients.

An additional feature of this invention provides a significantly purified form of the said proteinaceous cell surface component of the bacterium *S.pneumoniae*, having an epitope present in at least 96% of strains of said bacterium. A preferred embodiment of this feature is a 67,000 dalton protein or fragment thereof containing such an epitope. It is to be preferred that an epitope of said component or part thereof is present in more than 99% of the strains of *S.pneumoniae*, and is only present in said bacterium.

I have generated a MAb that specifically recognized an epitope of a proteinacous cell surface component of the *S.pneumoniae* common to more than 96% of all strains of said bacterium. The use of this MAb for immunodiagnosis and typing is disclosed.

DETAILED DESCRIPTION OF THE INVENTION

The production of a monoclonal antibody directed against a common protein of S.pneumoniae.

The strains of bacteria and culture conditions

S.pneumoniae strains were obtained from clinical isolates from Children's Hospital of Eastern Ontario, Ottawa, Laboratoire de la Santé Publique de Quebec, Sainte-Anne de Bellevue, and Trinidad. S.pneumoniae was grown on chocolate agar plates supplemented with 1% ISOVITALEX ® (BBL, Cockeysville, Md.) overnight at 37° C., in an atmosphere containing 5% $CO_2$. The resulting cultures were stored in brain heart infusion broth containing 20% glycerol at −70° C.

Protein preparation

The extraction of the proteins from the bacteria was performed using SABCOSYL. Whole cells (from 50 plates) suspended in phosphate buffered saline PBS (45 ml) were heat-killed at 56° C. for 20 minutes and centrifuged at 3600 RPM Sorvall SS-34 rotor with Rmax=10.70 cm for 30 minutes using a fixed angle. The pellet was resuspended in 14 ml of 10 mM Hepes buffered water, pH7.4. The cells were then sonicated using a Vibra Cell sonicator, 4 times ×30 seconds pulse at 50%, 30 seconds between each sonication. The suspension was centrifuged at 3500 RPM in a Sorvall SS-34 rotor with Rmax=10.70 cm for 20 minutes. The supernatant was centrifuged once more to get it more clear. It was then transferred to a rigid wall polycarbonate tube, and ultracentrifuged at 28.8K (28,800 RPM) for 60 minutes, 7° C. using a 50.2 Ti rotor. The supernatant was discarded and the pellet resuspended in 1 ml of 10 mM Hepes buffered water. Fifteen seconds of sonication was necessary to resuspended the pellet. One ml of 2% N-Lauryl Sarcosine (SARCOSYL) in 10 mM hepes buffered water was added to the suspension and the tube was gently shaken for approximately 3 minutes at room temperature to mix. The suspension was ultracentrifuged again, at 28.8 K for 60 minutes at 7° C. The protein content of the supernatant was determined by the BIO-RAD protein assay (Bio-Rad Laboratories, Mississauga, Ontario, Canada).

Immunization of mice

A BALB/c mouse was inoculated sub-cutaneously with 5 µg of S.pneumoniae strain Trinidad 810062 proteins from the sarcosyl extraction, combined with 25 µg of Quil A. Three weeks later, the mouse was reinjected subcutaneously with 5 µg proteins and 25 µg Quil A. Eight days before the hybridoma production, the mouse was given 5 µg proteins and 25 µg Quil A, sub-cutaneously. Six and three days before the fusion, the mouse received 5 µg of the same protein preparation, but without Quil A, and the injection was done intraperitoneally. Serum was obtained from the immunized mouse by cardiac puncture before spleen removal.

Fusion procedure

Hybridomas were produced according to a modification of the methods described by Fazekas De St. Groth and Scheidegger, J. Immunol Methods, vol. 35, 1-21 (1986). Spleen cells from immunized mouse and nonsecreting, HGPRT deficient, mouse myeloma cells P3×63 Ag 8.653 were fused in a ratio 10:1 in Dulbecco modified Eagle's medium (DMEM, Flow Laboratories, Mississauga, Ontario, Canada) containing 50% (w/v) polyethylene glycol 1000 (T.J. Baker Chemical Co., Phillipsburg, N.J.). The fused cells (0.1 ml, $1.5 \times 10^5$ cells/ml) were portioned into 96-well tissue culture plates (Costar plastics, Vineland, N.J.) which contained a feeder layer of $4 \times 10^3$ murine peritoneal exudate cells (macrophages). The suspensions of cells were grown in DMEM that were supplemented with 20% bovine calf serum (Gibco), 2 mM L-glutamine (Sigma Chemical Co., St. Louis, Mo.), and 50 µg/ml gentamicin (Sigma) in the presence of hypoxanthine, aminopterin, and thymidine (HAT) selection medium. All cultures were checked on day six for the presence of clones and the medium was changed. Supernatants of wells containing growing clones were tested on day twelve by ELISA for MAb directed against S.pneumoniae antigens. The cells that were producing antibody were subcloned through limiting dilution. Subclones that were selected were grown either as ascites according to the method of Brodeur et al, J. Immunol Methods, 71, 265-272 (1984) or in vitro for freezing in liquid nitrogen.

Immunoglobulin class determination

The supernatant from the cells producing antibodies were tested against affinity purified anti-mouse immunoglobulin (Southern Biotech) using the ELISA method.

Enzyme-Linked Immunosorbent Assay (ELISA) Procedure

Screening of resulting supernatants for MAbs directed against S.pneumoniae was performed as described by Brodeur et al, J. Med. Microbiol, vol. 15, 1-9, (1982). The antigen (0.1 ml) containing 0.75 µg protein in 0.05M carbonate buffer at pH 9.6 was portioned into each well of a High-binding microtiter plate (Flow). The plate was incubated overnight at room temperature to permit the adsorption of the antigen. The plate was then washed with PBS containing 0.02% Tween-20 (Sigma) and 150 µl of 0.5% bovine serum albumin (BSA, Sigma) in PBS was added to each well. The plate was incubated at 37° C. for 30 minutes. The BSA was discarded and the plate was washed and the test supernatants were added. The positive control was a standard serum. After a one hour incubation at 37° C., the plate was washed three times. This was followed with the addition of 0.1 ml alkaline phosphatase-conjugated goat anti-mouse immunoglobulins (Miles Laboratories, Elkart, Ind.) diluted 1:1000 in PBS containing 3% BSA. The plate was incubated at 37° C. for an additional 1 hour. The plate was then washed and 0.1 ml of a 10% diethanolamine solution (pH 9.8), containing 1 mg/ml p-nitrophenylphosphate (Sigma) was added. The plate was allowed to stand for sixty minutes. The absorbance was then determined spectrophotometrically using a DYNATECH ® microplate reader MR 600 at 410nm. Readings greater than 0.1 were scored as positive, indicating the presence of antibodies directed against S.pneumoniae.

SDS-polyacrylamide gel electrophoresis (PAGE)

Resolution of proteins was achieved through electrophoresis on sodium dodecyl sulfate (SDS) 0.75 mm thick slab mini gels according to the method described by Laemmli, Nature, vol. 227, 680-685 (1970). A 10% acrylamide (Bio-Rad) resolving gel and a 4.0% stacking gel were utilized. Cell lysates used on the gels were prepared by sonication, SARCOSYL extraction or heat-killed whole cell preparation. Lysates were mixed with sample buffer (62.5 mM Tris-HCl) pH 6.8, 1% (v/v) glycerol, 2% (w/v) SDS, 0.5% (v/v) 2-mercaptoethanol and 0.5% (w/v) bromophenol blue) and heated for 5 min. at 100° C. Aliquots of 15 µl containing 7.5 µg of protein were applied to each gel lane. Electrophoresis was carried out at 100 V constant voltage until the bromophenol blue tracking dye entered the separating gel. At this time, the voltage was then increased to 200 V. The gels were stained with Coomassie blue dye and then destained following the method of Weber and Osborn in *J.Biol. Chem.* vol. 244, 4406-4412 (1969). The protein standards used were: Phosphorylase b (97,000), Bovine serum albumin (66,200), ovalbumin (45,000), carbonic anhydrase (28,000), Soybean Trypsine Inhibitor (20,100), α-lactalbumin (14,200) (Bio-Rad Laboratories, Mississauga, Ontario, Canada).

Immunoblotting procedure

The proteins were transferred electrophoretically from the SDS-PAGE gel to nitrocellulose paper (Bio-Rad) by the method described by Towbin et al., *Proc. Natl. Acad. Sci.*, vol. 76, 4350-4354 (1979). A constant current of 66 mA was applied to the gel-nitrocellulose paper sandwich for 15 minutes. This was done in an electroblot buffer of 25 mM Tris-HCl, 192 mM glycine and 20% (v/v) methanol at pH 8.1. The proteins transferred onto the blot were either stained with amido black or detected by an enzyme immunoassay. The detection of bacterial antigens was performed by soaking the paper in PBS solution containing 1% milk for 30 minutes in order to block non-specific protein binding sites. The paper was then incubated with mouse hyperimmune sera at 37° C. for 1 hour. The sheet was washed three times with PBS followed by a 1 hour incubation at 37° C. with peroxidase-conjugated goat anti-mouse immunoglobulins (Cappel, Cochranville, Pa.) diluted 1:1000 in PBS containing 3% BSA. The sheet was once again washed three times and the blots were soaked in a solution of o-dianisidine prepared as described by Towbin et al (supra).

Dot-enzyme immunoassay

A dot-enzyme immunoassay was used for a quick method of screening several MAbs against a large number of *S.pneumoniae* strains. The strains were grown on chocolate agar plates overnight and an aliquot of approximately $3 \times 10^9$ bacteria/ml was prepared in PBS. A small amount of the suspension, approximately 40 µl was applied to a nitrocellulose paper using a DOT-BLOT apparatus (Bio-Rad Laboratories, Mississauga, Ontario, Canada). The dot nitrocellulose paper was then processed following the procedure described in the immunoblotting procedure.

Enzymatic treatment of proteins

Nitrocellulose paper with transferred proteins (see immunoblotting procedure) was treated with 3 different enzymes before being processed with the MAb. The paper was soaked in a 1.25 mg/ml Proteinase K solution for ½ hour, a 150 µg/ml Trypsin solution for 2 hours, or in a 1 mg/ml Chymotrypsin solution for 2 hours. The nitrocellulose paper was then processed with the MAb as described in the immunoblotting procedure. These treated papers were observed for the disappearance of the protein band. The normal immunoblot, without enzymatic treatment, was used as a positive control.

Properties of monoclonal antibodies

More than 450 hybrid clones were obtained by fusing sensitized mouse spleen cells with $P_3 \times 63$ Ag8.653 cells. The screening for the MAbs in the hybridoma culture supernatants was performed by ELISA, utilizing the homologous immunizing *S.pneumoniae* SARCOSYL extract as the coating antigens. Every positive hybrid clone supernatant was further tested against several other strains of *S.pneumoniae*. Eight hybridoma cell lines that demonstrated different patterns of reactivity in ELISA were obtained (see Table 1).

TABLE 1

| | | Characterization of monoclonal antibodies directed against *S. pneumoniae* antigens. | | | |
|---|---|---|---|---|---|
| | Clone | Immunoglobulin Class/subclass | O.D. at 410 mm | Antigen recognized | Specificity to *S. pneumoniae* |
| 1) | 1G-4 | IgG$_1$ | 0.154 | protein, approximately 72 KDa | few strains only |
| 2) | 2D-4 | IgM | >2.000 | carbohydrate | non-specific |
| 3) | 2G-1 | IgM | 0.136 | N/A | N/A |
| 4) | 4A-9 | IgG$_3$ | >2.000 | carbohydrate | non-specific |
| 5) | 6B-5 | IgA | 0.294 | carbohydrate | non-specific |
| 6) | 6E-9 | IgM/IgG$_1$ | 1.000 | proteins. approximately 67 KDa and 100 KDa carbohydrate | non-specific |
| 7) | 11E-1 | IgG1 | 0.124 | protein, approximately 67 KDa | yes |
| 8) | 13H-8 | IgG2A | 0.364 | protein, approximately 72 KDa | homol. strain only |

MAb 11E-1 was the only clone that was very specific to all the strains of *S.pneumoniae*. It was also directed against a protein. This MAb was subcloned twice by limiting dilution and the class and subclass were determined using affinity purified anti-mouse immunoglobulikn (Southern Biotech) in an ELISA test. This clone was then identified as 11E-1H-3/F-11 but 11E-1 kept as the official designation.

Clone 11E-1 was deposited with the American Type Culture Collection, 12301 Parklawn Dr., Rockville, Md. on Feb. 4, 1993, under the ATCC accession number HB 11262.

Identification of antibody-specific epitopes on the antigen

The Western immunoblotting technique was used to ascertain the specific antigen to which each MAb binds. The mouse hyperimmune serum that was used as positive control, detected all the major proteins present in strains of S.pneumoniae.

Seven of the eight MAbs reacted with antigens transferred from the SDS-PAGE to nitrocellulose paper. The remaining MAb was too weak to react. Three different proteins were recognized by the MAbs with apparent molecular weights of 100,000, 72,000 and 67,000 daltons. In addition a number of very low molecular weight carbohydrates were recognized.

Binding properties of monoclonal antibody 11E-1

To determine whether clone 11E-1 was directed against the cell surface exposed epitope of the 67,000 dalton protein, or part thereof, hybridoma culture supernatants containing the MAbs were incubated with live intact S.pneumoniae bacterial cells. The bacteria were then washed twice with PBS and incubated with $^{125}$I-labelled goat anti-mouse Ig (Dupont) and pelleted.

The bacterial cell-bound $^{125}$I was counted using a 1282 Compugamma. Fewer than 3000 cpm were obtained using negative controls. These data represent the mean of triplicate determinations.

Supernatant containing the MAb 11E-1 showed counts between 5 to 9 times the negative controls containing no MAb, indicating that the component is surface accessible.

Specificity of monoclonal antibody 11E-1

The initial ELISA characterization showed 11E1 reacted only with S.pneumoniae strains. A dot-enzyme immunoassay was used for a rapid method of screening this MAb against numerous bacterial strains. The MAb 11E-1 reacted specifically with 118 S.pneumoniae strains and only cross reacted with one strain of Streptococcus sanguis type I (Table II)

TABLE II

| Specificity of monoclonal antibody 11E-1 | |
|---|---|
| Bacterial strains | Reactivity by DOT-blot[1] |
| S. pneumoniae | 118/123 |
| other Streptococcus sp. | 1/29[2] |
| N. meningitidis | 0/8 |
| other Neisseria sp. | 0/7 |
| E. coli | 0/7 |
| S. aureus | 0/1 |
| H. influenzae | 0/1 |
| K. pneumoniae | 0/1 |
| S. epidermidis | 0/2 |

[1]Number of positive/Number of Strains
[2]Positive strain is S. sanquis 1 ID 12315 from LSPQ, Ste-Anne de Bellevue, Quebec Note: Of the 5 strains of S.pneumoniae that are not recognized by DOT-assay, 4 have been tested by immunoblot indicating that the 67KDa.

Preparation of Protein Antigen Extract

Several preparative methods of protein extracts have been utilized, especially for SDS-PAGE gel electrophoresis. The sarcosyl extraction has been described previously. An additional method involved the sonication of the bacteria. Approximately 10" bacteria were suspended in 5ml PBS and heat-killed for 20 minutes at 56° C. Using a SONIFIER CELL DISRUPTOR 350, (pulse was set at 50%), the cells were sonicated 3×5 minutes, being kept on ice during the entire procedure. The suspension was then centrifuged for 20 minutes at 25000 RPM using a 70 Til rotor run at 10° C. The supernatant was kept and the protein content determined by the BIO-RAD protein assay. Whole cell extract was also used, 50 µl of 10% SDS was added to the bacterial suspension, which was then boiled for 20 minutes and centrifuged.

I claim:
1. The 11E-1 monoclonal antibody produced by the hybridoma with ATCC accession number HB 11262.
2. The hybridoma cell line with ATCC accession number HB 11262.

* * * * *